US007176336B2

(12) United States Patent
Maughon et al.

(10) Patent No.: US 7,176,336 B2
(45) Date of Patent: Feb. 13, 2007

(54) PROCESS FOR THE SYNTHESIS OF UNSATURATED ALCOHOLS

(75) Inventors: Bob R. Maughon, Midland, MI (US); Kenneth A. Burdett, Midland, MI (US); Zenon Lysenko, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 316 days.

(21) Appl. No.: 10/940,403

(22) Filed: Sep. 14, 2004

(65) Prior Publication Data

US 2005/0080301 A1 Apr. 14, 2005

Related U.S. Application Data

(60) Provisional application No. 60/509,908, filed on Oct. 9, 2003.

(51) Int. Cl.
*C07C 29/00* (2006.01)
*C07C 33/025* (2006.01)
*C07C 33/03* (2006.01)

(52) U.S. Cl. .................. 568/876; 568/857; 568/875; 568/877; 568/909.5

(58) Field of Classification Search .................. None
See application file for complete search history.

(56) References Cited

U.S. PATENT DOCUMENTS

| 4,545,941 | A | 10/1985 | Rosenburg |
| 4,560,792 | A | 12/1985 | Banasiak |
| 4,772,758 | A | 9/1988 | Kaufhold |
| 4,943,397 | A | 7/1990 | Johnson |
| 5,143,885 | A | 9/1992 | Warwel et al. |
| 5,218,131 | A | 6/1993 | Warwel et al. |
| 5,312,940 | A | 5/1994 | Grubbs et al. |
| 5,342,985 | A | 8/1994 | Herrmann et al. |
| 5,352,812 | A | 10/1994 | Feldman et al. |
| 5,539,060 | A | 7/1996 | Tsunogae et al. |
| 5,932,664 | A | 8/1999 | Chen et al. |
| 6,060,572 | A | 5/2000 | Gillis et al. |
| 6,111,149 | A * | 8/2000 | Schwab et al. .............. 568/904 |
| 6,156,692 | A | 12/2000 | Nubel et al. |
| 6,191,324 | B1 * | 2/2001 | Guram et al. ................ 568/909 |
| 6,197,894 | B1 | 3/2001 | Sunaga et al. |
| 6,369,283 | B1 * | 4/2002 | Guram et al. ............. 568/909.5 |
| 6,635,768 | B1 | 10/2003 | Herrmann et al. |

FOREIGN PATENT DOCUMENTS

| DE | A1-281594 | 8/1990 |
| DE | 4107056 A1 | 9/1992 |
| DE | 100 41 345 | 3/2002 |
| EP | 0 084 437 A1 | 7/1983 |
| EP | 0 099 572 B2 | 2/1984 |
| EP | 0 328 230 | 8/1989 |
| JP | J 56 077243 | 6/1981 |
| JP | J 03 066725 A | 3/1991 |
| WO | WO 91/14665 | 10/1991 |
| WO | WO 93/20111 | 10/1993 |
| WO | WO 96/04289 | 2/1996 |
| WO | WO 97/06185 | 2/1997 |
| WO | WO 99/00397 | 1/1999 |
| WO | WO 99/22866 | 5/1999 |
| WO | WO 00/15339 | 3/2000 |
| WO | WO 00/58322 | 10/2000 |
| WO | WO 00/71554 | 11/2000 |
| WO | WO 02/076920 | 10/2002 |
| WO | WO 03/093215 | 11/2003 |
| WO | WO 04/037754 | 5/2004 |

OTHER PUBLICATIONS

Database CAPLUS on STN, Acc. No. 1992:567369, Brodowsky et al., Journal of Biological Chemistry (1992), 267(21), p. 14738-45 (abstract).*
Ahn, Yu Mi et al., "A Convenient Method for the Efficient Removal of Ruthenium Byproducts Generated During Olefin Metathesis Reactions", Organic Letters, vol. 3, pp. 1411-1413 (2001).
Biermann, Ursula et al., "New Synthesis with Oils and Fats as Renewable Raw Materials for the Chemical Industry", Angewandte Chemie Int. Ed., vol. 39, pp. 2207-2224 (2000).
Buchowicz, W. et al., "Catalytic Activity and Selectivity of $Ru(=CHPh)Cl_2(PCy_3)_2$ in the Metathesis of Linear Alkenes", Journal of Molecular Catalysis A; Chemical, vol. 148, pp. 97-103 (1999).
Derwent Abstract, AN 1991-015326 (DD 281594) (1991).
Dowden, James et al., "Olefin Metathesis in Non-Degassed Solvent Using a Recyclable, Polymer Supported Alkylideneruthenium", Chemical Communications, pp. 37-38 (2001).
Gessler, Simon et al., "Synthesis and Metathesis Reactions of a Phosphine-Free Dihydroimidazole carbine Ruthenium Complex", Tetrahedron Letters, vol. 41, pp. 9973-9976 (2000).
Kingsbury, Jason et al., "A Recyclable Ru-Based Metathesis Catalyst", Journal of the American Chemical Society, vol. 121, pp. 791-799 (1999).

(Continued)

*Primary Examiner*—Brian Davis
(74) *Attorney, Agent, or Firm*—Marie F. Zuckerman

(57) ABSTRACT

A process of preparing an unsaturated alcohol (olefin alcohol), such as, a homo-allylic mono-alcohol or homo-allylic polyol, involving protecting a hydroxy-substituted unsaturated fatty acid or fatty acid ester, such as methyl ricinoleate, derived from a seed oil, to form a hydroxy-protected unsaturated fatty acid or fatty acid ester; homo-metathesizing or cross-metathesizing the hydroxy-protected unsaturated fatty acid or fatty acid ester to produce a product mixture containing a hydroxy-protected unsaturated metathesis product; and deprotecting the hydroxy-protected unsaturated metathesis product under conditions sufficient to prepare the unsaturated alcohol. Preferably, methyl ricinoleate is converted by cross-metathesis or homo-metathesis into the homo-allylic mono-alcohol 1-decene-4-ol or the homo-allylic polyol 9-octadecene-7,12-diol, respectively.

25 Claims, No Drawings

OTHER PUBLICATIONS

Mandelli, Dalmo et al., "Ethenolysis of Esters of Vegetable Oils: Effect of $B_2O_3$ Addition to $Re_2O_7/SiO_2O_3$-$SnBu_4$ and $CH_3ReO_3/SiO_2Al_2Al_2O_3$ Metathesis Catalysts", Journal of the American Oil Chemical Society, vol. 73, pp. 229-232 (1996).

Maynard, Heather et al., "Purification Technique for the Removal of Ruthenium from Olefin Metathesis Reaction Products", Tetrahedron Letters, vol. 40, pp. 4137-4140 (1999).

Nubel, P.O. et al., "A Convenient Catalyst System Employing $RuCl_3$ or $RuBr_3$ for Metathesis of Acyclic Olefins", Journal of Molecular Catalysis A: Chemical, vol. 145, pp. 323-327 (1999).

Paquette, Leo et al., "A Convenient Method for Removing All Highly-Colored Byproducts Generated During Olefin Metathesis Reactions", Organic Letters, vol. 2, pp. 1259-1261 (2000).

Refvik, M.D. et al., "Ruthenium-Catalyzed Metathesis of Vegetable Oils", Journal of the American Oil Chemical Society, vol. 76, pp. 93-98 (1999).

Warwel, Siegfried et al., "Polymers and Surfactants on the Basis of Renewable Resources", CHEMOSPHERE, vol. 43, pp. 39-48 (2001).

Yao, Qingwei, "A Soluble Polymer-Bound Ruthenium Carbene Complex: A Robust and Reusable Catalyst for Ring-Closing Olefin Metathesis", Angewandte Chemie Intl. Ed., vol. 39, pp. 3896-3898 (2000); (German version: Yao; Qingwei, "Ein löslicher, polymergebundener rutheniumcarbenkomplex: ein robuster und wiederverwendbarer Katalysator für Ringschluss-Olefinmetathesen", Angewandte Chemie, vol. 112, pp. 4060-4063 (2000).

"Integrated Chemical Processes for Industrial Utilization of Seed Oils", filed in the United States of America on Apr. 17, 2003, U.S. Appl. No. 10/508,805; Applicant; Zenon Lysenko, et al.

"Metathesis of Unsaturated Fatty Acid Esters or Unsaturated Fatty Acids with Lower Olefins", filed in the United States of America on Feb. 27, 2002, U.S. Appl. No. 10/469,321; Applicant; Thomas H. Newman, et al.

Burdett, Kenneth A., "Renewable Monomer Feedstocks via Olefin Metathesis: Fundamental Mechanistic Studies of Methyl Oleate Ethenolysts with the First-Generation Grubbs Catalyst", ORGANOMETALLICS, vol. 23, pp. 2027-2047, 2004.

Burdett, Kenneth A., et al., "Stabilization of Olefin Metathesis Product Mixtures", filed in the United States of America on Mar. 21, 2005, U.S. Appl. No. 10/528,472.

* cited by examiner

PROCESS FOR THE SYNTHESIS OF UNSATURATED ALCOHOLS

CROSS REFERENCE TO RELATED APPLICATION

This application claims the benefit of U.S. Provisional Application Ser. No. 60/509,908, filed Oct. 9, 2003.

This invention was made with US Government support under Award Number DE-FC36-01ID14213 (formerly known as Award Number DE-FC07-01ID14213) awarded by the Department of Energy. The United States Government has certain rights in the invention.

BACKGROUND OF THE INVENTION

This invention pertains to a metathesis process for producing unsaturated alcohols (olefin alcohols).

Unsaturated alcohols, such as homo-allylic and allylic alcohols, are useful intermediates in the preparation of synthetic rubbers, surfactants, fragrances, and thermoplastic polyurethanes.

In recent years the chemical industry has directed attention towards replacing petroleum-based chemical feedstocks with non-petroleum-based chemical feedstocks. Along these lines investigations have focused on converting natural and genetically-modified seed oils into useful industrial organic chemicals. It is known, for example, that unsaturated fatty acid esters derived from seed oils can undergo cross-metathesis reactions with lower olefins, such as $C_{2-8}$ olefins, in the presence of a metathesis catalyst to form reduced-chain olefins and reduced-chain unsaturated esters. International patent application publication WO-A-96/04289, for example, discloses such metathesis reactions wherein the catalyst contains monodentate ligands, that is, ligands having one binding site to a central catalytic metal. As an illustrative example, methyl oleate is disclosed to undergoes cross-metathesis with ethylene (ethenolysis) in the presence of dichloro-3,3-diphenylvinyl-carbene-bis(tricyclohexylphosphine)ruthenium (II), to form 1-decene, a reduced chain α-olefin, and methyl 9-decenoate, a reduced chain unsaturated ester. Homo-metathesis reactions are also disclosed, wherein one molecule of unsaturated fatty acid ester is metathesized with a molecule of identical unsaturated fatty acid ester. As an example, methyl oleate is disclosed to undergo homo-metathesis to form 9-octadecene and dimethyl-1,18-octadec-9-enedioate.

The metathesis of hydroxy-substituted unsaturated fatty acids and fatty acid esters derived from seed oils also produces unsaturated alcohols (olefin alcohols) that are different from the reactant hydroxy-substituted fatty acids and fatty acid esters. Such unsaturated alcohol products may be value-added depending upon market conditions and end-uses. Cross-metathesis typically produces an unsaturated mono-alcohol; whereas homo-metathesis typically produces an unsaturated polyol. As an example, the cross-metathesis of methyl 12-hydroxy-octadec-9-eneoate (methyl ricinoleate) with ethylene produces a homo-allylic alcohol, namely, 1-decene-4-ol, and an unsaturated ester, namely, methyl 9-decenoate. Disadvantageously, however, when a hydroxy-substituted unsaturated fatty acid or fatty acid ester is metathesized, a catalyst turnover number is achieved that tends to be low for practical applications. For the purposes of this invention, the term "catalyst turnover number" shall refer to the number of moles of metathesis product formed per mole of metathesis catalyst employed.

In view of the above, it would be desirable to discover an improved process of homo-metathesizing or cross-metathesizing a hydroxy-substituted unsaturated fatty acid or fatty acid ester for the purpose of preparing an unsaturated alcohol product that is different from the hydroxy-substituted unsaturated fatty acid or fatty acid ester reactant. It would be more desirable if the unsaturated alcohol product was an allylic mono-alcohol or allylic polyol, or a homo-allylic mono-alcohol or homo-allylic polyol. It would be even more desirable if such a process exhibited an improved catalyst turnover number, as compared with present day processes. An improved catalyst turnover number should enhance the potential for commercializing the metathesis of hydroxy-substituted unsaturated fatty acids and fatty acid esters, thereby providing a route to useful industrial organic chemicals via non-petroleum-based chemical feedstocks, such as, natural or genetically-modified seed oils.

SUMMARY OF THE INVENTION

In one aspect, this invention provides for a novel metathesis process of preparing an unsaturated alcohol (olefin alcohol). This novel metathesis process comprises (a) contacting a hydroxy-protected unsaturated fatty acid or fatty acid ester, derived from a hydroxy-substituted unsaturated fatty acid or fatty acid ester, with a metathesis catalyst, and optionally a lower olefin, under metathesis conditions sufficient to produce at least one hydroxy-protected unsaturated product that is different from the hydroxy-protected unsaturated fatty acid or fatty acid ester; and (b) deprotecting the hydroxy-protected unsaturated product under conditions sufficient to produce the unsaturated alcohol. The terms "hydroxy-protected" and "deprotecting" are described in detail hereinafter.

In another aspect, this invention provides for an integrated process for producing an unsaturated alcohol comprising (a) treating a hydroxy-substituted unsaturated fatty acid or fatty acid ester with a hydroxy-protection reagent under conditions sufficient to produce a hydroxy-protected unsaturated fatty acid or fatty acid ester; (b) contacting the hydroxy-protected unsaturated fatty acid or fatty acid ester with a metathesis catalyst, and optionally a lower olefin, under metathesis conditions sufficient to produce a product mixture comprising at least one hydroxy-protected unsaturated product that is different from the hydroxy-protected unsaturated fatty acid or fatty acid ester; (c) optionally, separating the hydroxy-protected unsaturated product from the product mixture; and (d) deprotecting the hydroxy-protected unsaturated product under conditions sufficient to prepare the unsaturated alcohol.

The novel processes of this invention find utility in the preparation of unsaturated alcohols including, for example, allylic mono-alcohols and allylic polyols and homo-allylic mono-alcohols and homo-allylic polyols, which can be used as intermediates in the manufacture of synthetic rubbers, surfactants, fragrances, thermoplastic polyurethanes, and other useful industrial chemicals. Advantageously, the processes of this invention produce value-added unsaturated mono-alcohols and unsaturated polyols from non-petroleum-based chemical feedstocks derived from seed oils. As compared with prior art processes, the processes of this invention advantageously provide for improved catalyst turnover number, which correlates with improved yield of unsaturated alcohol product per mole of metathesis catalyst employed.

In a third aspect, this invention comprises a novel compound comprising 9-octadecene-7,12 diol, which finds utility in the manufacture of surfactants and thermoplastic polyurethanes.

DETAILED SUMMARY OF THE INVENTION

The novel inventions described herein pertain to metathesis processes for producing unsaturated alcohols (olefin alcohols), for example, allylic mono-alcohols, allylic polyols, homo-allylic mono-alcohols, and homo-allylic polyols, starting from a hydroxy-substituted unsaturated fatty acid or fatty acid ester, typically derived from a natural or genetically-modified seed oil. Preliminary to the metathesis process of this invention, the hydroxy-substituted unsaturated fatty acid or fatty acid ester is treated to form a hydroxy-protected unsaturated fatty acid or fatty acid ester. For the purposes of this invention, the term "hydroxy-protected" means that each hydroxy-substituent of the hydroxy-substituted unsaturated fatty acid or fatty acid ester has been reacted with a hydroxy-protection reagent to form the corresponding fatty acid or fatty acid ester having one or more protective functionalities that are less reactive, and preferably non-reactive, in the metathesis process, as compared with the hydroxy functionality. Thereafter, the hydroxy-protected unsaturated fatty acid or fatty acid ester is subjected to homo-metathesis or cross-metathesis. After metathesis, the protective functionality is typically removed to regenerate hydroxy functionality in the corresponding metathesis product(s). In this manner, unsaturated alcohols including, for example, allylic mono-alcohols, allylic polyols, homo-allylic mono-alcohols, and homo-allylic polyols, can be prepared by metathesis with improved catalyst turnover number. More specifically, unsaturated mono-alcohols can be prepared by cross-metathesis; while unsaturated polyols can be prepared by homo-metathesis, as described in detail hereinafter.

In a first aspect, therefore, this invention provides for a novel metathesis process of preparing an unsaturated alcohol. This novel metathesis process comprises (a) contacting a hydroxy-protected unsaturated fatty acid or fatty acid ester, derived from a hydroxy-substituted unsaturated fatty acid or fatty acid ester, with a metathesis catalyst, and optionally a lower olefin, under metathesis conditions sufficient to produce at least one hydroxy-protected unsaturated product that is different from the hydroxy-protected unsaturated fatty acid or fatty acid ester; and (b) deprotecting the hydroxy-protected unsaturated product under conditions sufficient to produce the unsaturated alcohol.

In a preferred embodiment of this first aspect, the hydroxy-protected unsaturated fatty acid or fatty acid ester is a hydroxy-protected $C_{8-60}$ unsaturated fatty acid or fatty acid ester. In another preferred embodiment, the hydroxy-protected unsaturated fatty acid or fatty acid ester is an acetate, ether, or carbonate-substituted unsaturated fatty acid or fatty acid ester.

In a second aspect, this invention provides for an integrated process for producing an unsaturated alcohol comprising (a) treating a hydroxy-substituted unsaturated fatty acid or fatty acid ester with a hydroxy-protection reagent under conditions sufficient to produce a hydroxy-protected unsaturated fatty acid or fatty acid ester; (b) contacting the hydroxy-protected unsaturated fatty acid or fatty acid ester with a metathesis catalyst, and optionally a lower olefin, under metathesis conditions sufficient to produce a product mixture comprising at least one hydroxy-protected unsaturated product that is different from the hydroxy-protected unsaturated fatty acid or fatty acid ester; (c) optionally, separating the hydroxy-protected unsaturated product from the product mixture; and (d) deprotecting the hydroxy-protected unsaturated product under conditions sufficient to prepare the unsaturated alcohol.

In a preferred embodiment of this second aspect, the process comprises (a) treating a hydroxy-substituted $C_{8-60}$ unsaturated fatty acid or fatty acid ester with a hydroxy-protection reagent under conditions sufficient to produce a hydroxy-protected $C_{8-60}$ unsaturated fatty acid or fatty acid ester; (b) contacting the hydroxy-protected $C_{8-60}$ unsaturated fatty acid or fatty acid ester with a metathesis catalyst, and optionally a $C_{2-8}$ olefin, under metathesis conditions sufficient to produce a product mixture comprising at least one hydroxy-protected olefin that is different from the hydroxy-protected $C_{8-60}$ unsaturated fatty acid or fatty acid ester; (c) optionally, separating the hydroxy-protected olefin from the product mixture; and (d) deprotecting the hydroxy-protected olefin under conditions sufficient to prepare the unsaturated alcohol.

In a more preferred embodiment, the product mixture further comprises an unsaturated mono-ester or an unsaturated diester. In a most preferred embodiment of cross-metathesis, the lower olefin is ethylene; and the unsaturated mono-ester is an $\alpha,\omega$-unsaturated ester. In a most preferred embodiment of homo-metathesis, the unsaturated diester is an unsaturated $\alpha,\omega$-diester.

In an optional aspect of this invention, the unsaturated mono-ester or unsaturated diester can be converted, typically via hydrolysis, to the corresponding unsaturated monocarboxylic acid or unsaturated polyacid, respectively.

In yet another more preferred embodiment, this invention pertains to a process of preparing a homo-allylic polyol. In this aspect, the process comprises (a) treating a hydroxy-substituted $C_{8-60}$ unsaturated fatty acid or fatty acid ester with a hydroxy-protection reagent under conditions sufficient to produce a hydroxy-protected $C_{8-60}$ unsaturated fatty acid or fatty acid ester; (b) contacting the hydroxy-protected $C_{8-60}$ unsaturated fatty acid or fatty acid ester with a metathesis catalyst under homo-metathesis conditions sufficient to produce a product mixture comprising an unsaturated diester and a homo-allylic polyol having protected hydroxy groups; (c) optionally, separating the homo-allylic polyol having protected hydroxy groups from the product mixture; and (d) deprotecting the homo-allylic polyol having protected hydroxy groups under conditions sufficient to produce the homo-allylic polyol. In a most preferred embodiment each hydroxy group is protected by an acetate functionality.

In yet another more preferred embodiment, this invention pertains to a process of preparing a homo-allylic mono-alcohol. In this aspect, the process comprises (a) treating a hydroxy-substituted $C_{8-60}$ unsaturated fatty acid or fatty acid ester with a hydroxy-protection reagent under conditions sufficient to produce a hydroxy-protected $C_{8-60}$ unsaturated fatty acid or fatty acid ester; (b) contacting the hydroxy-protected $C_{8-60}$ unsaturated fatty acid or fatty acid ester with a $C_{2-8}$ olefin in the presence of a metathesis catalyst under cross-metathesis conditions sufficient to produce a product mixture comprising an unsaturated ester and a homo-allylic mono-alcohol having a protected hydroxy group; (c) optionally, separating the homo-allylic mono-alcohol having the protected hydroxy group from the product mixture; and (d) deprotecting the homo-allylic mono-alcohol having the protected hydroxy group under conditions sufficient to prepare the homo-allylic mono-alcohol. In a most preferred embodiment of this invention, the $C_{2-8}$ olefin is ethylene; and the hydroxy group is protected by an acetate functionality.

In another most preferred embodiment of the above-identified processes, the hydroxy-substituted $C_{8-60}$ unsaturated fatty acid or fatty acid ester comprises, respectively, ricinoleic acid (12-hydroxy octadec-9-enoic acid) or methyl ricinoleate (methyl 12-hydroxy-octadec-9-enoate). In this preferred embodiment, the unsaturated mono-alcohol is a homo-allylic mono-alcohol comprising 1-decene-4-ol, and the unsaturated polyol is a homo-allylic polyol comprising 9-octadecene-7,12-diol.

In a final aspect, this invention pertains to a composition comprising 9-octadecene-7,12-diol. The composition can be prepared by a process comprising (a) converting 12-hydroxy-octadec-9-eneoic acid (ricinoleic acid) or an ester thereof into a corresponding 12-hydroxy-protected octadec-9-eneoic acid or ester; (b) homo-metathesizing the 12-hydroxy-protected acid or ester in the presence of a metathesis catalyst under metathesis conditions sufficient to prepare a hydroxy-protected 9-octadecene-7,12 diol; and (c) deprotecting the hydroxy-protected unsaturated diol under conditions sufficient to prepare 9-octadecene-7,12-diol.

Any hydroxy-substituted unsaturated fatty acid or fatty acid ester can be suitably employed to prepare the hydroxy-protected unsaturated fatty acid or fatty acid ester. An unsaturated fatty acid comprises an extended carbon chain containing at least one carbon-carbon double bond and terminating in a carboxylic acid group. Typically, the unsaturated fatty acid will contain greater than about 8 carbon atoms, preferably, greater than about 10 carbon atoms, and more preferably, greater than about 12 carbon atoms. Typically, the unsaturated fatty acid will contain less than about 60 carbon atoms, preferably, less than about 40 carbon atoms, and more preferably, less than about 35 carbon atoms. At least one carbon-carbon double bond is present along the carbon chain, this double bond usually occurring about the middle of the chain, but not necessarily. Unsaturated fatty acids containing two or more carbon-carbon double bonds are also suitably employed. The unsaturated fatty acid chain may be straight or branched and is required to contain at least one hydroxy-substituent anywhere along the chain. In one preferred embodiment, the hydroxy substituent is bound to a carbon atom adjacent to a carbon atom in the double bond, such that the hydroxy substituent is located on an allylic carbon. In another preferred embodiment, the hydroxy substituent is bound to a carbon atom one carbon removed from a carbon atom in the double bond, such that the hydroxy substituent is located on a homo-allylic carbon atom.

Other substituents may also be present on the unsaturated fatty acid or fatty acid ester chain, provided that such substituents are substantially inert with respect to the metathesis process. Non-limiting examples of suitable substituents, other than the required hydroxy functionality, include alkyl moieties, preferably $C_{1-10}$ alkyl moieties, for example, methyl, ethyl, propyl, and butyl; cycloalkyl moieties, preferably, $C_{4-8}$ cycloalkyl moieties, for example, cyclopentyl and cyclohexyl; monocyclic aromatic moieties, preferably, $C_6$ aromatic moieties, that is, phenyl; arylalkyl moieties, preferably, $C_{7-16}$ arylalkyl moieties, for example, benzyl; and alkylaryl moieties, preferably, $C_{7-16}$ alkylaryl moieties, for example, tolyl, ethylphenyl, and xylyl; as well as halogen, preferably, chloro and bromo, ether, ester, aldehyde, and keto substituents, and the like. Non-limiting examples of suitable unsaturated fatty acids include ricinoleic acid (12-hydroxy-cis-octadec-9-enoic), auricolic acid, avenoleic acid, axillarenic acid, coriolic acid, densipolic acid, helenynolic acid, isoricinoleic acid, kamlolenic acid, lesquerolic acid, ricinelaidic acid, strophanthus acid, and mixtures thereof. Ricinoleic acid is preferred.

Likewise, any hydroxy-substituted unsaturated fatty acid ester may be employed to prepare the hydroxy-protected unsaturated fatty acid ester. The hydroxy-substituted unsaturated fatty acid segment of the ester may assume any of the forms described hereinabove. The alcohol segment of the ester comprises a monohydric, dihydric, or polyhydric alcohol that is capable of condensing with the fatty acid to form the fatty acid ester. Typically, the alcohol segment of the ester contains at least one carbon atom. Typically, the alcohol segment of the ester contains less than about 20 carbon atoms, preferably, less than about 12 carbon atoms, and more preferably, less than about 8 carbon atoms. The carbon atoms may be arranged in a straight or branched structure, and may be substituted with a variety of substituents, such as those previously disclosed hereinabove in connection with the fatty acid, including the aforementioned alkyl, cycloalkyl, aryl, arylalkyl, alkylaryl, hydroxy, halogen, ether, ester, aldehyde, and keto substituents. Preferably, the alcohol segment comprises a straight-chain or branched $C_{1-12}$ alkanol. A preferred alcohol segment is the trihydric alcohol glycerol, the fatty acid esters of which are known as "glycerides" and obtainable from seed oils. Other preferred alcohols include $C_{1-8}$ lower alkanols, such as methanol and ethanol, the fatty acid esters of which may be obtained through transesterification of the corresponding fatty acid glycerides derived from seed oils. Preferred seed oils include castor, musk, and mellon oils, as well as Isano oil, and Kamala oil.

In the process of this invention, the hydroxy-substituted unsaturated fatty acid or fatty acid ester is first treated to convert each hydroxy substituent present into a hydroxy-protected substituent. Suitable protective groups include any organic functionality that exhibits lower reactivity in metathesis processes as compared with hydroxy. Suitable non-limiting examples of protective groups include esters, ethers, silyl ethers, sulfonate esters, and carbonates. Conventional organic reactions, known to those of skill in the art, can be employed to convert the hydroxy substituent(s) into one of the aforementioned protective groups. The unsaturated fatty acids or fatty acid esters derived therefrom are referred-to herein as "hydroxy-protected unsaturated fatty acids or fatty acid esters."

A suitable resource describing the reaction conditions typically employed to protect hydroxy functionalities is found in the following citation, incorporated herein by reference: T. W. Greene, *Protective Groups in Organic Synthesis*. John Wiley & Sons, New York, 1981, pp 10–118. As an example, hydroxy groups can be reacted with carboxyl halides or anhydrides, such as acetic anhydride, to prepare the corresponding ester, e.g., acetate. Likewise, hydroxy groups can be condensed with alcohols or alkyl halides to form ethers, or reacted with dialkyl carbonates to form carbonate substituents. As an example, the hydroxy-substituted fatty acid or fatty acid ester may be combined with acetic anhydride in an appropriate solvent, such as a halogenated alkane or pyridine or a combination thereof, and a catalyst, such as 4-(N,N-dimethylamino)pyridine, at a temperature ranging between about ambient, taken as 21° C., and about 100° C. at ambient or autogenous pressure for a sufficient time to form the corresponding acetate-protected fatty acid or fatty acid ester, which is then separated from the reaction mixture by conventional methods, such as, extraction methods. Preferably, the reactions converting the hydroxy substituents into hydroxy-protected substituents are reversible allowing the protective group or groups to be removed, reverting therefore to the original hydroxy functionality.

The homo-metathesis process of this invention requires contacting one molecule of hydroxy-protected unsaturated fatty acid or fatty acid ester with a second molecule of the same. Cross-metathesis in this invention requires contacting one molecule of hydroxy-protected unsaturated fatty acid or fatty acid ester with a molecule of different olefin, preferably, a lower olefin. For the purposes of this invention, the term "lower olefin" shall refer to an organic compound having at least 2 carbon atoms and typically less than about 10 carbon atoms, and containing at least one carbon-carbon double bond. Generally, only one carbon-carbon double bond is preferred, which may however be a terminal double bond or an internal double bond. The lower olefin may be substituted with one or more substituents along the carbon chain, provided that the substituents are essentially inert with respect to the metathesis process. Suitable substituents include, without limitation, alkyl, preferably, $C_{1-6}$ alkyl; cycloalkyl, preferably, $C_{3-6}$ cycloalkyl; as well as hydroxy, ether, keto, aldehyde, and halogen functionalities. Non-limiting examples of suitable lower olefins include ethylene, propylene, butene, butadiene, pentene, hexene, the various isomers thereof, and as well, the higher homologues thereof up to about an 8 carbon chain. Preferably, the lower olefin is a $C_{2-8}$ olefin. More preferably, the lower olefin is a $C_{2-6}$ olefin, even more preferably, a $C_{2-4}$ olefin, and most preferably, ethylene or propylene.

In cross-metathesis processes, the hydroxy-protected unsaturated fatty acid or fatty acid ester and lower olefin may be fed to a metathesis reactor in any amounts that provide for an operable metathesis process. The molar ratio of lower olefin to hydroxy-protected unsaturated fatty acid or fatty acid ester can vary depending upon the specific reactants and specific reactor design. The following molar ratios are set forth as a guide, but this invention should not be limited to the ratios disclosed herein. Typically, the molar ratio of lower olefin to hydroxy-protected unsaturated fatty acid or fatty acid ester is greater than about 0.8/1.0, preferably, greater than about 0.9/1.0. Typically, the molar ratio of lower olefin to hydroxy-protected unsaturated fatty acid or fatty acid ester is less than about 3.0/1.0, preferably, less than about 2.0/1.0. Depending upon the specific reagents, other molar ratios may be suitable. With ethylene, for example, a significantly higher molar ratio is possible, because the self-metathesis of ethylene produces only ethylene again. Accordingly, the molar ratio of ethylene to hydroxy-protected unsaturated fatty acid or fatty acid ester may range from greater than about 0.8/1 to typically less than about 20/1.

The hydroxy-protected unsaturated fatty acid or fatty acid ester is generally provided as a liquid at the process temperature, and it is generally preferred to be used neat, that is, without a diluent or solvent. Optionally, however, a solvent may be employed with the hydroxy-protected unsaturated fatty acid or fatty acid ester. A solvent may be desirable, for instance, where a liquid lower olefin and the hydroxy-protected unsaturated fatty acid or fatty acid ester are not entirely miscible, and both then can be solubilized in a suitable solvent. The solvent can be any thermally stable and chemically stable liquid that has an acceptable miscibility with the hydroxy-protected unsaturated fatty acid or fatty acid ester. The term "thermally stable" means that the solvent does not substantially decompose at the process temperature. The term "chemically stable" means that the solvent is substantially non-reactive with the metathesis reagents and products, and also implies that the solvent does not coordinate with the metathesis catalyst in a manner that substantially inhibits catalyst performance. The term "miscible" means that the solvent and hydroxy-protected unsaturated fatty acid or fatty acid ester form a homogeneous solution essentially without phase separation. Non-limiting examples of suitable solvents include aromatic hydrocarbons, such as benzene, toluene, xylenes, and the like; chlorinated aromatic hydrocarbons, preferably chlorinated benzenes, such as chlorobenzene and dichlorobenzene; alkanes, such as pentane, hexane, cyclohexane, and the like; and chlorinated alkanes, such as methylene chloride and chloroform. If a solvent is used, then any amount can be employed, provided that the metathesis process proceeds as desired. Generally, the concentration of the hydroxy-protected unsaturated fatty acid or fatty acid ester in the solvent is greater than about 0.05 M, preferably, greater than about 0.5 M. Generally, the concentration of hydroxy-protected unsaturated fatty acid or fatty acid ester in the solvent is less than about the saturation concentration, preferably, less than about 5.0 M.

When the hydroxy-protected unsaturated fatty acid or fatty acid ester and optional lower olefin are provided in liquid phase, then the metathesis process is preferably conducted under an inert atmosphere, so as to minimize interference by oxygen. The inert atmosphere may comprise any gas or gaseous mixture that is essentially inert with respect to the metathesis process, including, without limitation, helium, neon, argon, nitrogen, and mixtures thereof. If the lower olefin is a gas, then the lower olefin may be fed to the reactor as an essentially pure gas or, optionally, diluted with an essentially inert gaseous diluent, such as, helium, neon, argon, nitrogen, and mixtures thereof. Suitable concentrations of lower olefin in the diluent gas typically are greater than about 5 mole percent, and preferably, greater than about 10 mole percent, based on the total moles of lower olefin and gaseous diluent. Suitable concentrations are typically less than about 95 mole percent.

As a further option, a stabilizing ligand may be added to the metathesis reaction mixture. The stabilizing ligand may be any molecule or ion that promotes catalyst stability in the metathesis process, as measured, for example, by increased activity or extended catalyst lifetime. Non-limiting examples of stabilizing ligands include tri(alkyl)phosphines, such as tricyclohexylphosphine, tricyclopentylphosphine, and tributylphosphine; tri(aryl)phosphines, such as tri(phenyl)phosphine, tri(methylphenyl)phosphine (ortho, meta, and para substituted isomers), and tri(p-fluorophenyl)phosphine; diarylalkylphosphines, for example, diphenylcyclohexylphosphine; dialkylarylphosphines, such as dicyclohexylphenylphosphine; ethers, such as anisole; pyridines, such as 2,6-dimethylpyridine, 2-t-butylpyridine, 2,6-difluoropyridine, and 2-methylpyridine; phosphine oxides, such as triphenylphosphine oxide; as well as phosphinites, phosphonites, phorphoramidites, and mixtures of any of the aforementioned ligands. Preferably, the stabilizing ligand is a tri(alkyl)phosphine, more preferably, tri(cyclohexyl)phosphine. The quantity of stabilizing ligand can vary depending upon the specific catalyst employed and its specific ligand components. Typically, the molar ratio of stabilizing ligand to metathesis catalyst is greater than about 0.05/1, and preferably, greater than about 0.5/1. Typically, the molar ratio of stabilizing ligand to metathesis catalyst is less than about 2.0/1, and preferably, less than about 1.5/1.

The metathesis catalyst employed in the process of this invention may comprise any known catalyst for homo-metathesis or cross-metathesis processes. Suitable metathesis catalysts containing monodentate ligands are described in international patent application publications WO 96/04289, WO 97/06185, WO 00/58322, WO 00/71554, and WO 00/15339, incorporated herein by reference. Other metathesis catalysts may comprises chelating ligands. The term "chelating ligand" refers to a ligand, whether neutral molecule or ion, which has a plurality of moieties, each of which is capable of binding to the catalytic metal of the catalyst. Typically, the metathesis catalyst comprises ruthenium or osmium as catalytic metal; ruthenium is preferred. Preferably, the metathesis catalyst is represented by the following formula:

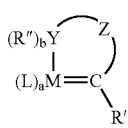

(I)

wherein M is Ru or Os; each L is independently selected from neutral and anionic ligands in any combination that balances the bonding and charge requirements of M; a is an integer, preferably from 1 to about 4, which represents the total number of ligands L; R' is selected from hydrogen, straight-chain or branched alkyl, cycloalkyl, aryl, and substituted aryl radicals; Y is an electron donor group, otherwise known as a Lewis base, of an element from Group 15 or 16 of the Periodic Table, as referenced by the IUPAC in *Nomenclature of Inorganic Chemistry: Recommendations 1990*, G. J. Leigh, Editor, Blackwell Scientific Publications, 1990; Y being more preferably O, S, N, or P; each R" is independently selected from hydrogen, alkyl, cycloalkyl, aryl, and substituted aryl radicals sufficient to satisfy the valency of Y, preferably such that Y is formally neutral; b is an integer, preferably 0 to about 2, representing the total number of R" radicals; and Z is an organic diradical that is bonded to both Y and the carbene carbon (C) so as to form a bidentate ligand, which ligand in connection with the M atom forms a ring of from about 4 to about 8 atoms. A bidentate ligand has two binding sites to the metal atom.

More preferably, each L is independently selected from the group consisting of halides, most preferably, fluoride, chloride, bromide, and iodide; cyanide, thiocyanate, phosphines of the formula $PR_3$, amines of the formula $NR_3$, water and ethers of the formula $OR_2$, thioethers of the formula $SR_2$, and ligands having the formulas II and III hereinafter:

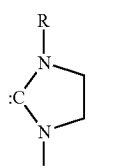 and (II)

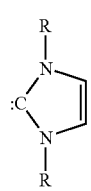

(III)

wherein each R in any of the aforementioned formulas is independently selected from the group consisting of hydrogen, alkyl, preferably, $C_{1-15}$ alkyl; cycloalkyl, preferably, $C_{3-8}$ cycloalkyl; and aryl, preferably, $C_{6-15}$ aryl and $C_{6-15}$ substituted aryl radicals. Substituted aryl radicals may comprise any substituent that does not interfere with the metathesis process, such as, halogen, alkyl, ether, ester, and keto substituents. Mixtures of any of the aforementioned ligands L may be employed in any given species of formula I. More preferably, R' is selected from the group consisting of hydrogen, $C_{1-15}$ alkyl, $C_{3-8}$ cycloalkyl, and $C_{6-15}$ aryl radicals. More preferably, each R" is independently selected from the group consisting of $C_{1-15}$ alkyl, $C_{3-8}$ cycloalkyl, and $C_{6-15}$ aryl radicals. Preferably, Z is selected from the following diradicals: ethylene (IV), vinylene (V), phenylene (VI), substituted vinylenes (VII), substituted phenylenes (VIII), naphthylene (IX), substituted naphthylenes (X), piperazindiyl (XI), piperidiyl (XII):

(IV)

(V)

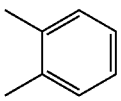

(VI)

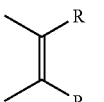

(VII)

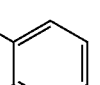

(VIII)

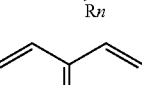

(IX)

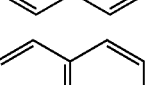

(X)

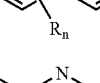

(XI)

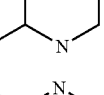

(XII)

wherein each R may be, as noted above, selected from hydrogen, alkyl, preferably, $C_{1-15}$ alkyl; cycloalkyl, preferably, $C_{3-8}$ cycloalkyl; and aryl, preferably, $C_{6-15}$ aryl, radicals; and wherein each n is an integer from 1 to about 4.

Preferred species of catalyst include:
bis(tricyclohexylphosphine)benzylidene ruthenium dichloride,
bis(tricyclohexylphosphine)benzylidene ruthenium dibromide,
bis(tricyclohexylphosphine)benzylidene ruthenium diiodide,
[(1,3-Bis-(2,4,6-trimethylphenyl)-2 imidazolidinylidene) dichloro(phenylmethylene)-(tricyclohexylphosphine)ruthenium)]
[(1,3-Bis-(2,4,6-trimethylphenyl)-2 imidazolidinylidene) dibromo(phenylmethylene)-(tricyclohexylphosphine)ruthenium)],
[(1,3-Bis-(2,4,6-trimethylphenyl)-2 imidazolidinylidene) diiodo(phenylmethylene)-(tricyclohexylphosphine)ruthenium)],
Dichloro[[2-(1-methylethoxy-α-O)phenyl]methylene-α-C] (tricyclohexylphosphine) ruthenium,
Dibromo[[2-(1-methylethoxy-α-O)phenyl]methylene-α-C] (tricyclohexylphosphine) ruthenium,
Diiodo[[2-(1-methylethoxy-α-O)phenyl]methylene-α-C] (tricyclohexylphosphine) ruthenium,
1,3-Bis-(2,4,6-trimethylphenyl)-2-imidazolidinylidene) dichloro(o-isopropoxyphenylmethylene)ruthenium,
1,3-Bis-(2,4,6-trimethylphenyl)-2-imidazolidinylidene)dibromo(o-isopropoxyphenylmethylene)ruthenium, and
1,3-Bis-(2,4,6-trimethylphenyl)-2-imidazolidinylidene)diiodo(o-isopropoxyphenylmethylene)ruthenium.

Most preferably, the catalyst is selected from the group consisting of:
1,3-Bis-(2,4,6-trimethylphenyl)-2-imidazolidinylidene) dichloro(o-isopropoxyphenylmethylene)ruthenium,
1,3-Bis-(2,4,6-trimethylphenyl)-2-imidazolidinylidene)dibromo(o-isopropoxyphenylmethylene)ruthenium,
1,3-Bis-(2,4,6-trimethylphenyl)-2-imidazolidinylidene)diiodo(o-isopropoxyphenylmethylene)ruthenium,
[(1,3-Bis-(2,4,6-trimethylphenyl)-2 imidazolidinylidene) dichloro(phenylmethylene)-(tricyclohexylphosphine)ruthenium)],
[(1,3-Bis-(2,4,6-trimethylphenyl)-2-imidazolidinylidene) dibromo(phenylmethylene)-(tricyclohexylphosphine)ruthenium)], and
[(1,3-Bis-(2,4,6-trimethylphenyl)-2 imidazolidinylidene) diiodo(phenylmethylene)-(tricyclohexylphosphine)ruthenium)].

Methods for synthesizing ruthenium and osmium carbene complexes are known to those skilled in the art. General methods can be found in the following references, incorporated herein by reference: (1) *Transition Metals in the Synthesis of Complex Organic Molecules* by L. S. Hegedus, University Science Books, 1994; (2) *Angew. Chem. Int. Ed. Eng.* 1995, 34, 2039–2041, by P. Schwab, M. B. France, J. W. Ziller and R. H. Grubbs, and (3) *Jason S. Kingsbury et al., Journal of the American Chemical Society*, 1999, 121, 791–799.

In another embodiment, the catalyst employed in the process of this invention may be bound to or deposited on a solid catalyst support. The solid catalyst support will render the catalyst heterogeneous, which simplifies catalyst recovery. In addition, the catalyst support may increase catalyst strength and attrition resistance. Suitable catalyst supports include, without limitation, silicas, aluminas, silica-aluminas, aluminosilicates, including zeolites and other crystalline porous aluminosilicates; as well as titanias, zirconia, magnesium oxide, carbon, and cross-linked reticular polymeric resins, such as functionalized cross-linked polystyrenes, e.g., chloromethyl-functionalized cross-linked polystyrenes. If a support is used, then generally the catalyst loading onto the support is greater than about 0.01 weight percent, and preferably, greater than about 0.05 weight percent catalytic metal, based on the total weight of the catalyst plus support. Generally, the catalyst loading is less than about 20 weight percent, and preferably, less than about 10 weight percent catalytic metal, based on the total weight of the catalyst and support.

The metathesis process of this invention can be conducted in accordance with conventional practices in the art. Any reactor suitably designed for such processes can be employed, including batch reactors, continuous stirred tank reactors, continuous flow fixed bed reactors, slurry reactors, fluidized bed reactors, and catalytic distillation reactors. Typically, the process temperature is greater than about 0° C., preferably, greater than about 20° C. Typically, the process temperature is less than about 150° C., preferably, less than about 120° C., and more preferably, less than about 90° C. Typically, with the use of a gaseous lower olefin, the olefin pressure is greater than about 5 psig (34.5 kPa), preferably, greater than about 10 psig (68.9 kPa), and more preferably, greater than about 45 psig (310 kPa). Typically, the lower olefin pressure is less than about 1,000 psig (6,895 kPa), preferably, less than about 750 psig (3,447 kPa), and more preferably, less than about 500 psig (2,758 kPa). When a diluent is used with the gaseous lower olefin, the aforementioned pressure ranges may also be suitably employed as the total pressure of olefin and diluent. The pressure in liquid phase homo-metathesis processes may range from autogenous to any convenient pressure of diluent gas.

The quantity of metathesis catalyst employed in the process of this invention comprises any quantity providing for an operable metathesis reaction. If the process is conducted in a batch reactor, the ratio of moles of hydroxy-protected unsaturated fatty acid or fatty acid ester to moles of metathesis catalyst is typically greater than about 10:1, preferably, greater than about 50:1, and more preferably, greater than about 100:1. Under batch conditions, the molar ratio of hydroxy-protected unsaturated fatty acid or fatty acid ester to metathesis catalyst is typically less than about 10,000,000:1, preferably, less than about 1,000,000:1, and more preferably, less than about 500,000:1. The contacting time of the reagents and catalyst in a batch reactor can be any duration, provided that the desired metathesis products are obtained. Generally, the contacting time is greater than about 5 minutes, and preferably, greater than about 10 minutes. Generally, the contacting time is less than about 25 hours, preferably, less than about 15 hours, and more preferably, less than about 10 hours.

If the process is conducted under continuous flow conditions, then the weight hourly space velocity, given in units of grams hydroxy-protected unsaturated fatty acid or fatty acid ester per gram catalyst per hour ($h^{-1}$), will determine the relative quantities of hydroxy-protected unsaturated fatty acid or fatty acid ester to catalyst employed, as well as the residence time in the reactor of the unsaturated starting compound. In a flow reactor, the weight hourly space velocity (WHSV) of the hydroxy-protected unsaturated fatty acid or fatty acid ester is typically greater than about 0.04 g per g catalyst per hour ($h^{-1}$), and preferably, greater than about 0.1 $h^{-1}$. Typically, the WHSV is less than about 100 $h^{-1}$, and preferably, less than about 20 $h^{-1}$. The flow of the lower olefin, which may be introduced into the reactor as a gas or a liquid stream, is adjusted so as to produce the desired ratio of olefin to hydroxy-protected unsaturated fatty acid or fatty acid ester.

When the process of this invention is conducted as described hereinabove, then at least one olefin product is formed that is different from the hydroxy-protected unsaturated fatty acid or fatty acid ester. In cross-metathesis, the products typically comprise an unsaturated ester and a hydroxy-protected olefin. The cross-metathesis of methyl 12-acetyl-octadec-9-eneoate with ethylene, for example, produces the unsaturated ester methyl 9-decenoate and the hydroxy-protected olefin 1-decene-4-acetate. In homo-metathesis, the products typically comprise an unsaturated diester and an olefin having a plurality of hydroxy-protected groups. The homo-metathesis of methyl 12-acetyl-octadec-9-eneoate, for example, produces the unsaturated diester dimethyl-1,18-octadec-9-enedioate and the hydroxy-protected olefin 9-octadecene 7,12-diacetate.

In the metathesis process of this invention, the conversion of hydroxy-protected unsaturated fatty acid or fatty acid ester can vary widely depending upon the specific reagent olefins, the specific catalyst, and specific process conditions employed. For the purpose of this invention, "conversion" is defined as the mole percentage of hydroxy-protected unsaturated fatty acid or fatty acid ester that is converted to products. Typically, the conversion is greater than about 5 mole percent, preferably, greater than about 25 mole percent, and more preferably, greater than about 40 mole percent. Likewise, the yield of olefin metathesis product, calculated as mole percentage of olefin metathesis product formed based on initial moles of hydroxy-protected unsaturated fatty acid or fatty acid ester, is typically greater than about 5 percent, preferably, greater than about 20 percent, and more preferably, greater than about 35 percent. More significantly, the catalyst turnover number obtained in the practice of this invention, is typically greater than about 400, preferably, greater than about 1,000, more preferably, greater than about 3,000, and most preferably, greater than about 6,000 moles of olefin metathesis product(s) formed per mole of catalyst employed.

Optionally, the hydroxy-protected unsaturated products obtained in the metathesis process of this invention may be separated from the metathesis reaction mixture by conventional organic chemistry methods known to those of skill in the art, including by extraction, distillation, crystallization, and the like. Moreover, the hydroxy-protected unsaturated products can be deprotected by methods known in the art to form the corresponding unsaturated alcohols (olefin alcohols). Preferred unsaturated alcohols are selected from the group consisting of homo-allylic mono-alcohols, homo-allylic polyols, allylic mono-alcohols, and allylic polyols. More preferred unsaturated alcohols are selected from the group consisting of homo-allylic mono-alcohols, most preferably 4-decene-1-ol, and homo-allylic polyols, most preferably 9-octadecene-7,12-diol. The homo-allylic mono-alcohols typically exhibit a chain length from about 5 to about 40 carbon atoms. The homo-allylic polyols typically exhibit a chain length from about 8 to about 60 carbon atoms.

Suitable deprotection conditions may be found, for example, in T. W. Greene, *Protective Groups in Organic Synthesis*, John Wiley & Sons, New York, 1981, pp 10–118, relevant sections of which are incorporated herein by reference. As an example, 1-decene-4-acetate and 9-octadecene-7,12-diacetate can be deprotected to form 1-decene-4-ol and 9-octadecene-7,12-diol, respectively. In addition, the unsaturated ester co-products can, if desired, be hydrolyzed by methods known in the art to the corresponding carboxylic acids. For example, methyl 9-decenoate and dimethyl 1,18-octadec-9-enedioate can be hydrolyzed to 9-decenoic acid and 1,18-octadec-9-enedicarboxylic acid, respectively. General conditions for the deprotection of acetate protecting groups can also be found in T. W. Greene, *Protective Groups in Organic Synthesis*, ibid.

The following examples are provided as illustrations of the processes of this invention, but should not be construed as limiting the invention in any manner. In light of the disclosure herein, those of skill in the art will recognize modifications in the reagents, catalyst, and metathesis process conditions that fall within the scope of this invention.

EXAMPLES 1–6

Methyl ricinoleate (12-hydroxy-octadec-9-eneoate) was hydroxy-protected by reaction with acetic anhydride to prepare methyl ricinoleate acetate (12-acetyl-octadec-9-eneoate) as follows. Methyl ricinoleate (77.0 g, 0.246 mol, 1.0 eq) was combined with methylene chloride (100 mL), pyridine (100 mL), acetic anhydride (37.73 g, 0.370 mol, 1.5 eq), and catalytic 4-(N,N-dimethylamino)pyridine (0.5 g), and the resulting mixture was heated to 35° C. in a 500 mL round bottom flask. The reaction flask was connected to a reflux condenser (cooled via chilled water) and the reaction was kept under a flow of nitrogen. The reaction was maintained under these conditions for 72 h, at which point it was cooled to room temperature. The resulting reaction mixture was extracted with an aqueous saturated solution of sodium bicarbonate (4×100 mL), aqueous hydrochloric acid (1 M; 4×100 mL), dried over magnesium sulfate, and concentrated in vacuo. Vacuum distillation over calcium hydride produced a clear oil. Methyl ricinoleate acetate was recovered and then treated over alumina (Aldrich activated basic alumina, Brockmann I, catalogue #19944-3) prior to use.

A cross-metathesis reaction was conducted with the alumina-treated methyl ricinoleate acetate and ethylene. The general procedure for the metathesis process was as follows. The treated methyl ricinoleate acetate (0.99 g; 2.81 mmol) was loaded into a reactor tube (Symyx PPR-48 slurry reactor). The reactor was sealed, and toluene (2.95 ml) was added to the reactor tube. The reactor was then brought to the desired temperature and pressure of ethylene. To the pressurized tube, a toluene solution (100 uL toluene) containing the catalyst was added. The molar ratio of methyl ricinoleate acetate to catalyst was 20,673/1. The following catalysts were tested:

C12GI—bis(tricyclohexylphosphine)benzylidene ruthenium dichloride

Br2GI—bis(tricyclohexylphosphine)benzylidene ruthenium dibromide

I2GI—bis(tricyclohexylphosphine)benzylidene ruthenium diiodide

C12GIC—dichloro[[2-(1-methylethoxy-α-O)phenyl]methylene-α-C](tricyclohexyl-phosphine) ruthenium Br2GIC—dibromo[[2-(1-methylethoxy-α-O)phenyl]methylene-α-C](tricyclohexyl-phosphine) ruthenium I2GIC—diiodo[[2-(1-methylethoxy-α-O)phenyl]methylene-α-C](tricyclohexylphosphine) ruthenium After 4 each reaction was quenched under pressure with excess butyl vinyl ether. The primary products were identified as 1-decene-4-acetate and methyl 9-decenoate. Each product mixture was analyzed by gas chromatography (GC) to determine the conversion of hydroxy-protected unsaturated fatty acid ester, the yield of olefin metathesis products, and the metathesis catalyst turnover number. Process conditions and results for each catalytic run are shown in Table 1 herein below.

TABLE 1

Cross-Metathesis of Methyl Ricinoleate Acetate with Ethylene

| Example | Catalyst[1] | T (° C.)/ P (psig) | % Conv MRAc[2] | Yield[3] | Catalyst Turnover Number[4] |
|---|---|---|---|---|---|
| 1 | Cl2GI | 30/60 | 7.43 | 7.23 | 1495 |
| " | " | 60/60 | 16.83 | 16.75 | 3463 |
| 2 | Br2G1 | 30/60 | 5.71 | 5.62 | 1163 |
| " | " | 60/60 | 11.93 | 11.85 | 2449 |
| 3 | I2G1 | 30/60 | 2.65 | 2.55 | 528 |
| " | " | 60/60 | 5.44 | 5.35 | 1106 |
| 4 | Cl2GIC | 30/60 | 13.13 | 13.05 | 2698 |
| " | " | 60/60 | 12.77 | 12.69 | 2623 |
| 5 | Br2GIC | 30/60 | 10.75 | 10.70 | 2212 |
| " | " | 60/60 | 10.72 | 10.65 | 2201 |
| 6 | I2GIC | 30/60 | 2.24 | 2.15 | 445 |
| " | " | 60/60 | 2.20 | 2.11 | 435 |

[1]Molar ratio of methyl ricinoleate acetate to catalyst = 20,673/1.
[2]% Conv MRAc = mole percentage of methyl ricinoleate acetate converted to products.
[3]Yield = mole percentage of 1-decene-4-ol acetate or methyl 9-decenoate formed, based on initial moles of MRAc used. Products are formed in equal amounts.
[4]Catalyst turnover number = moles of homo-allylic alcohol acetate formed per mole of catalyst.

From Table 1 it is seen that the cross-metathesis of a hydroxy-protected unsaturated fatty acid ester with ethylene yields a homo-allylic mono-alcohol acetate. The homo-allylic mono-alcohol acetate is deprotected by conventional methods to yield the corresponding homo-allylic monoalcohol, 1-decene-4-ol.

Comparative Experiments 1–6

The metathesis process of Examples 1–6 was repeated with the exception that the methyl ricinoleate was not hydroxy-protected and the molar ratio of methyl ricinoleate to catalyst was 4,140/1. The quantity of catalyst used in the comparative experiments was higher than in Examples 1–6 in order to achieve a reasonable level of ricinoleate conversion. The methyl ricinoleate was treated over alumina and then used directly in the metathesis process with the desired catalyst and under process conditions similar to those used in Examples 1–6. The primary products included the homo-allylic mono-alcohol 1-decene-4-ol and methyl 9-deceneoate. Since the hydroxy functionality was not protected, no deprotection step was conducted. Process conditions and results are shown in Table 2.

TABLE 2

Cross-Metathesis of Methyl Ricinoleate with Ethylene

| Comparative Experiment | Catalyst[1] | T (° C.)/ P (psig) | % MR Conv[2] | Yield[3] | Catalyst Turnover Number[4] |
|---|---|---|---|---|---|
| 1 | Cl2GI | 30/60 | 7.10 | 7.04 | 292 |
| " | " | 60/60 | 4.82 | 4.74 | 196 |
| 2 | Br2G1 | 30/60 | 8.11 | 8.04 | 333 |
| " | " | 60/60 | 7.09 | 7.02 | 290 |
| 3 | I2G1 | 30/60 | 1.26 | 1.20 | 50 |
| " | " | 60/60 | 0.90 | 0.83 | 34 |
| 4 | Cl2GIC | 30/60 | 8.51 | 8.44 | 349 |
| " | " | 60/60 | 7.10 | 7.01 | 290 |
| 5 | Br2GIC | 30/60 | 7.84 | 7.76 | 321 |
| " | " | 60/60 | 8.26 | 8.18 | 339 |
| 6 | I2GIC | 30/60 | 1.72 | 1.65 | 68 |
| " | " | 60/60 | 1.81 | 1.75 | 72 |

[1]Molar ratio of methyl ricinoleate to catalyst = 4,140/1.
[2]% Conv MR = mole percentage of methyl ricinoleate converted to products.
[3]Yield = mole percentage of 1-decene-4-ol or methyl 9-decenoate formed, based on initial moles of MR used. Products are formed in equal amounts.
[4]Catalyst turnover number = moles of homo-allylic alcohol formed per mole of catalyst.

When the comparative experiments in Table 2 are compared with the corresponding examples in Table 1, it is seen that use of a hydroxy-protected unsaturated fatty acid ester resulted in higher yield of metathesis products and a higher catalyst turnover number, as compared with using an unprotected hydroxy-substituted unsaturated fatty acid ester.

EXAMPLES 7–12

Metathesis processes were conducted on methyl ricinoleate acetate in a manner similar to that of Examples 1–6, with the exception that a different set of catalysts was tested. The primary reaction products comprised 1-decene-4-acetate and methyl 9-decenoate. The 1-decene-4-acetate is deprotected as in Examples 1–6 to yield the homo-allylic mono-alcohol 1-decene-4-ol. The catalysts are illustrated hereinafter; and the process conditions and results are shown in Table 3.

C12GII-[(1,3-Bis-(2,4,6-trimethylphenyl)-2 imidazolidinylidene) dichloro(phenyl-methylene)-(tricyclohexylphosphine)ruthenium Br2GII-[(1,3-Bis-(2,4,6-trimethylphenyl)-2 imidazolidinylidene) dibromo(phenyl-methylene)(tricyclohexylphosphine)ruthenium)]

12GII-[(1,3-Bis-(2,4,6-trimethylphenyl)-2 imidazolidinylidene) diiodo(phenylmethylene)-(tricyclohexylphosphine)ruthenium)]

C12GIIC-1,3-Bis-(2,4,6-trimethylphenyl)-2-imidazolidinylidene)dichloro(o-isopropoxyphenylmethylene)ruthenium Br2GIIC-1,3-Bis-(2,4,6-trimethylphenyl)-2-imidazolidinylidene)dibromo(o-isopropoxyphenylmethylene)ruthenium 12GIIC-1,3-Bis-(2,4,6-trimethylphenyl)-2-imidazolidinylidene)diiodo(o-isopropoxyphenylmethylene)ruthenium

TABLE 3

Cross-Metathesis of Methyl Ricinoleate Acetate with Ethylene

| Example | Catalyst[1] | T (° C.)/ P (psig) | % MRAc Conv[2] | Yield[3] | Catalyst Turnover Number[4] |
|---|---|---|---|---|---|
| 7 | Cl2GII | 60/60 | 42.97 | 27.70 | 5726 |
| " | " | 90/60 | 55.59 | 32.34 | 6686 |
| 8 | Br2GII | 60/250 | 22.87 | 21.89 | 4525 |
| " | " | 90/250 | 32.37 | 32.31 | 6679 |
| 9 | I2GII | 60/250 | 40.16 | 39.95 | 8258 |
| " | " | 90/250 | 41.16 | 41.40 | 8559 |

TABLE 3-continued

Cross-Metathesis of Methyl Ricinoleate Acetate with Ethylene

| Example | Catalyst[1] | T (° C.)/ P (psig) | % MRAc Conv[2] | Yield[3] | Catalyst Turnover Number[4] |
|---|---|---|---|---|---|
| 10 | Cl2GIIC | 60/60 | 43.71 | 26.99 | 5580 |
| " | " | 90/60 | 39.79 | 18.46 | 3817 |
| 11 | Br2GIIC | 60/250 | 36.52 | 35.16 | 7268 |
| " | " | 90/250 | 39.63 | 39.58 | 8181 |
| 12 | I2GIIC | 60/250 | 36.79 | 36.73 | 7593 |
| " | " | 90/250 | 30.28 | 30.22 | 6247 |

[1]Molar ratio of methyl ricinoleate acetate to catalyst = 20,673.
[2]% Conv MRAc = mole percentage of methyl ricinoleate acetate converted to products.
[3]Yield = mole percentage of 1-decene-4-ol acetate or methyl 9-decenoate formed, based on initial moles of MRAc used. Products are formed in equal amounts.
[4]Catalyst turnover number = moles of homo-allylic alcohol acetate formed per mole of catalyst.

From Table 3 it is seen that the cross-metathesis of a hydroxy-protected unsaturated fatty acid ester with ethylene yields a homo-allylic mono-alcohol acetate. The homo-allylic mono-alcohol acetate is deprotected by conventional methods to yield the corresponding homo-allylic monoalcohol, 1-decene-4-ol.

Comparative Experiments 7–12

The metathesis processes of Examples 7–12 were repeated with the exception that the methyl ricinoleate was not hydroxy-protected and the molar ratio of methyl ricinoleate to catalyst was 4,140/1. The methyl ricinoleate was treated over alumina and then used directly in the metathesis process using the same catalysts and process conditions as in Examples 7–12. The primary products included the homo-allylic mono-alcohol 1-decene-4-ol and methyl 9-deceneoate. Since the hydroxy functionality was not protected, no deprotection step was conducted. Process conditions and results are shown in Table 4.

TABLE 4

Cross-Metathesis of Methyl Ricinoleate with Ethylene

| Comparative Experiment | Catalyst[1] | T (° C.)/ P (psig) | % MR Conv[2] | Yield[3] | Catalyst Turnover Number[4] |
|---|---|---|---|---|---|
| 7 | Cl2GII | 60/60 | 84.93 | 78.54 | 3252 |
| " | " | 90/60 | 66.47 | 40.91 | 1693 |
| 8 | Br2GII | 60/250 | 89.39 | 87.91 | 3639 |
| " | " | 90/250 | 78.12 | 76.68 | 3174 |
| 9 | I2GII | 60/250 | 69.73 | 69.56 | 2880 |
| " | " | 90/250 | 42.88 | 42.66 | 1766 |
| 10 | Cl2GIIC | 60/60 | 77.50 | 65.78 | 2723 |
| " | " | 90/60 | 66.07 | 48.79 | 2020 |
| 11 | Br2GIIC | 60/250 | 94.75 | 93.40 | 3867 |
| " | " | 90/250 | 85.97 | 84.67 | 3505 |
| 12 | I2GIIC | 60/250 | 63.24 | 63.01 | 2608 |
| " | " | 90/250 | 40.99 | 40.74 | 1687 |

[1]Molar ratio of methyl ricinoleate to catalyst = 4,140/1.
[2]% Conv MR = mole percentage of methyl ricinoleate converted to products.
[3]Yield = mole percentage of 1-decene-4-ol or methyl 9-decenoate formed, based on initial quantity of MR used. Products are formed in equal amounts.
[4]Catalyst turnover number = moles of homo-allylic alcohol formed per mole of catalyst.

When the comparative experiments in Table 4 are compared with the corresponding examples in Table 3, it is seen that use of a hydroxy-protected unsaturated fatty acid ester resulted in a higher catalyst turnover number, as compared with using an unprotected hydroxy-substituted unsaturated fatty acid ester.

EXAMPLES 13–15

The impact of a protecting group on homo-metathesis (metathesis in the absence of lower olefin, e.g., ethylene) was evaluated. The general procedure for the homo-metathesis process was as follows. Methyl ricinoleate acetate (2.00 g; 5.60 mmol), which had been treated over alumina in the manner described in Example 1, was loaded into a glass vial with a stir bar and tetradecane (0.20 g) as an internal standard. To the glass vial, a toluene solution containing C12GII catalyst, [(1,3-Bis-(2,4,6-trimethylphenyl)-2 imidazolidinylidene) dichloro(phenyl-methylene)-(tricyclohexylphosphine)ruthenium, was added where the mole ratio of methyl ricinoleate acetate to catalyst was varied from 5,000:1 to 100,000:1. Samples were removed at set intervals and quenched with excess butyl vinyl ether. Analysis was accomplished by GC to determine conversion of the methyl ricinoleate acetate and the catalyst turnover number to dimethyl-1,18-octadec-9-enedioate (moles of dimethyl-1,18-octadec-9-enedioate produced/mole catalyst). Results are presented in Table 5.

TABLE 5

Homo-metathesis of Methyl Ricinoleate Acetate with Cl2GII

| Example | (Methyl Ricinoleate Acetate/Catalyst) Mole Ratio | Time (min) | % Methyl Ricinoleate Acetate Conv[1] | Catalyst Turnover Number[2] |
|---|---|---|---|---|
| 13 | 5000 | 233 | 51.1 | 1278 |
| " | " | 1350 | 52.2 | 1305 |
| 14 | 40060 | 240 | 45.0 | 9014 |
| " | " | 1300 | 48.7 | 9755 |
| 15 | 100200 | 239 | 5.0 | 2506 |
| " | " | 1300 | 10.12 | 5072 |

[1]% Methyl Ricinoleate Acetate Conv. = mole percentage of methyl ricinoleate acetate converted to products.
[2]Catalyst turnover number = moles of dimethyl-1,18-octadec-9-enedioate produced per mole catalyst From Table 5 it is seen that the homo-metathesis of a hydroxy-protected unsaturated fatty acid ester yields a diol acetate, dimethyl-1,18-octadec-9-ene dioate. Hydrolysis of the diol acetate by conventional methods yields the corresponding 1,18-octadec-9-ene dicarboxylic acid. Additionally, the process produces an equal yield of homo-allylic diol diacetate, 9-octadecene-7,12 diol diacetate, which after deprotection to remove the acetate groups yields the homo-allylic diol 9-octadecene-7,12-diol.

Comparative Experiments 13–15

Examples 13–15 were repeated, with the exception that no protection of the hydroxy functionality was employed. Thus, methyl ricinoleate was used in place of methyl ricinoleate acetate, and the general procedure for the metathesis process was as follows. An alumina-treated methyl ricinoleate (2.00 g; 5.60 mmol) was loaded into a glass vial with a stir bar and tetradecane (0.20 g) as an internal standard. To the glass vial, a toluene solution containing C12GII catalyst, [(1,3-Bis-(2,4,6-trimethylphenyl)-2 imidazolidinylidene) dichloro(phenyl-methylene)-(tricyclohexylphosphine)ruthenium, was added where the mole ratio of methyl ricinoleate to catalyst was varied from 5,000 to 100,000:1. Samples were removed at set intervals and quenched with excess butyl vinyl ether. Analysis was accomplished by GC to determine conversion of the methyl ricinoleate and total turnovers to dimethyl-1,18-octadec-9-enedioate (moles of dimethyl-1,18-octadec-9-enedioate produced/mole catalyst). Results are presented in Table 6.

TABLE 6

Homometathesis of Methyl Ricinoleate with Cl2GII

| Comparative Experiment | (Methyl Ricinoleate/Catalyst) Mole ratio | Time (min) | % Methyl Ricinoleate Conv[1] | Catalyst Turnover Number[2] |
|---|---|---|---|---|
| 13 | 5000 | 234 | 48.9 | 1223 |
| " | " | 1350 | 49.6 | 1240 |
| 14 | 40300 | 243 | 24.1 | 4856 |
| " | " | 1300 | 26.3 | 5299 |
| 15 | 100100 | 238 | 0.01 | 5 |
| " | " | 1300 | 7.01 | 3500 |

[1]% Methyl Ricinoleate Conv. = mole percentage of methyl ricinoleate converted to products.
[2]Catalyst turnover number = moles of dimethyl-1,18-octadec-9-enedioate produced per mole catalyst.

The beneficial impact of the acetate protecting group is clearly demonstrated in the results from Examples 13–15 versus the Comparative Experiments 13–15. For Examples 14–15 and Comparative Experiments 14–15, higher conversions and turnovers are seen at both time intervals when the acetate protecting group is used. Only in Example 13 and Comparative Experiment 13 are similar results seen, but this results from both systems reaching equilibrium conversion (theoretical maximum near 50% conversion) due to an excessive amount of added catalyst. As catalyst loading is lowered, the improved catalyst performance can be observed when the protecting group is utilized. The highest demonstrated turnovers, 9755, are observed in Example 14 where the acetate protecting group is incorporated.

What is claimed is:

1. A process of preparing an unsaturated alcohol comprising (a) contacting a hydroxy-protected unsaturated fatty acid or fatty acid ester, derived from a hydroxy-substituted unsaturated fatty acid or fatty acid ester, with a metathesis catalyst, and optionally a lower olefin, under metathesis conditions sufficient to produce at least one hydroxy-protected unsaturated product that is different from the hydroxy-protected unsaturated fatty acid or fatty acid ester; and (b) deprotecting the hydroxy-protected unsaturated product under conditions sufficient to produce the unsaturated alcohol.

2. The process of claim 1 wherein the hydroxy-substituted unsaturated fatty acid or fatty acid ester comprises a hydroxy-substituted $C_{8-60}$ unsaturated fatty acid or fatty acid ester.

3. The process of claim 1 wherein the hydroxy-protected unsaturated fatty acid or fatty acid ester comprises a hydroxy-protected $C_{8-60}$ unsaturated fatty acid or fatty acid ester.

4. The process of claim 1 wherein the fatty acid is selected from the group consisting of ricinoleic acid, auricolic acid, avenoleic acid, axillarenic acid, coriolic acid, densipolic acid, helenynolic acid, isoricinoleic acid, kamlolenic acid, lesquerolic acid, ricinelaidic acid, strophanthus acid, and mixtures thereof.

5. The process of claim 1 wherein the hydroxy-protected unsaturated fatty acid or fatty acid ester is hydroxy-protected with an ester, ether, sulfonate ester, silyl ether, or carbonate functionality.

6. The process of claim 1 wherein the unsaturated fatty acid ester is derived from glycerol or a $C_{1-8}$ alkanol.

7. The process of claim 1 wherein the lower olefin is a $C_{2-8}$ olefin.

8. The process of claim 1 wherein a lower olefin is used, and wherein the ratio of lower olefin to hydroxy-protected unsaturated fatty acid or fatty acid ester is greater than about 0.8/1 and less than about 20/1.

9. The process of claim 1 wherein the metathesis catalyst is represented by the formula:

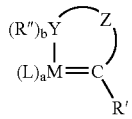

wherein M is Ru or Os; each L is independently selected from neutral and anionic ligands in a combination that balances the bonding and charge requirements of M; a is an integer from 1 to about 4; R' is selected from hydrogen, alkyl, cycloalkyl, aryl, and substituted aryl radicals; Y is an element from Group 15 or 16 of the Periodic Table; each R" is independently selected from hydrogen, alkyl, cycloalkyl, aryl, and substituted aryl radicals sufficient to satisfy the valency of Y; b is an integer from 0 to about 2; and Z is an organic diradical that is bonded to both Y and the carbene carbon (C) so as to form a bidentate ligand, which ligand in connection with the M atom forms a ring of from about 4 to about 8 atoms.

10. The process of claim 9 wherein each L is independently selected from the group consisting of fluoride, chloride, bromide, iodide; cyanide, thiocyanate, phosphines of the formula $PR_3$, amines of the formula $NR_3$, water and ethers of the formula $OR_2$, thioethers of the formula $SR_2$, and ligands having the formulas hereinafter:

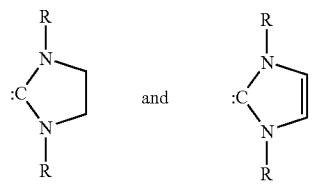

wherein each R in any of the above formulas is independently selected from the group consisting of hydrogen, $C_{1-15}$ alkyl, $C_{3-8}$ cycloalkyl, $C_{6-15}$ aryl, and $C_{6-15}$ substituted aryl radicals.

11. The process of claim 9 wherein Z is selected from the group consisting of: ethylene (IV), vinylene (V), phenylene (VI), substituted vinylenes (VII), substituted phenylenes (VIII), naphthylene (IX), substituted naphthylenes (X), piperazindiyl (XI), piperidiyl (XII), as shown in the formulas below:

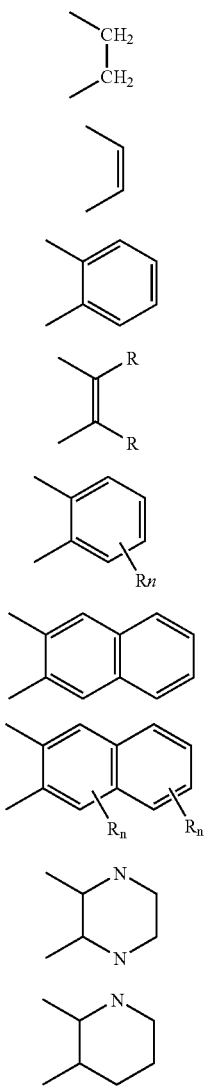

(IV)
(V)
(VI)
(VII)
(VIII)
(IX)
(X)
(XI)
(XII)

wherein each R is independently selected from hydrogen, $C_{1-15}$ alkyl, $C_{3-8}$ cycloalkyl, and $C_{6-15}$ aryl radicals and $C_{6-15}$ substituted aryl radicals; and wherein each n is an integer from 1 to about 4.

12. The process of claim 9 wherein M is ruthenium, and optionally, wherein L is selected from halides and trialkylphosphines, and Z is phenylene.

13. The process of claim 1 wherein the metathesis catalyst is selected from the group consisting of:
bis(tricyclohexylphosphine)benzylidene ruthenium dichloride,
bis(tricyclohexylphosphine)benzylidene ruthenium dibromide,
bis(tricyclohexylphosphine)benzylidene ruthenium diiodide,
[(1,3-Bis-(2,4,6-trimethylphenyl)-2 imidazolidinylidene) dichloro(phenyl-methylene)(tricyclohexylphosphine) ruthenium)],
[(1,3-Bis-(2,4,6-trimethylphenyl)-2 imidazolidinylidene) dibromo(phenyl-methylene)(tricyclohexylphosphine) ruthenium)],
[(1,3-Bis-(2,4,6-trimethylphenyl)-2 imidazolidinylidene) diiodo(phenylmethylene)-(tricyclohexylphosphine)ruthenium),
Dichloro[[2-(1-methylethoxy-α-O)phenyl]methylene-α-C](tricyclohexylphosphine) ruthenium,
Dibromo[[2-(1-methylethoxy-α-O)phenyl]methylene-α-C](tricyclohexylphosphine) ruthenium,
Diiodo[[2-(1-methylethoxy-α-O)phenyl]methylene-α-C] (tricyclohexylphosphine) ruthenium,
1,3-Bis-(2,4,6-trimethylphenyl)-2-imidazolidinylidene) dichloro(o-isopropoxyphenylmethylene)ruthenium,
1,3-Bis-(2,4,6-trimethylphenyl)-2-imidazolidinylidene) dibromo(o-isopropoxyphenylmethylene)ruthenium, and
1,3-Bis-(2,4,6-trimethylphenyl)-2-imidazolidinylidene) diiodo(o-isopropoxyphenylmethylene)ruthenium.

14. The process of claim 1 wherein a stabilizing ligand is added to the metathesis step.

15. The process of claim 14 wherein the stabilizing ligand is selected from the group consisting of trialkylphosphines, triarylphosphines, diarylalkylphosphines, aryldialkylphosphines, ethers, pyridines, phosphine oxides, phosphinites, phosphonites, phosphoramidites, and mixtures thereof.

16. The process of claim 1 wherein the metathesis step is conducted at a temperature greater than about 0° C. and less than about 150° C. and at a total pressure greater than about 5 psig (34.5 kPa) and less than about 1,000 psig (6,895 kPa).

17. The process of claim 1 wherein the unsaturated alcohol is selected from the group consisting of homo-allylic mono-alcohols, homo-allylic polyols, allylic mono-alcohols, and allylic polyols.

18. The process of claim 1 wherein the hydroxy-substituted unsaturated fatty acid ester is methyl ricinoleate; a lower olefin comprising ethylene is employed in the metathesis step; the cross-metathesis products comprise 1-decene-4-acetate and methyl 9-decenoate; and the deprotected product comprises 1-decene-4-ol.

19. The process of claim 1 wherein the hydroxy-substituted unsaturated fatty acid ester is methyl ricinoleate; the homo-metathesis products comprise 9-octadecene-7,12-diacetate and 1,18-dimethyloctadec-9-enedioate; and the deprotected product comprises 9-octadecene-7,12-diol.

20. The process of claim 1 wherein the metathesis product mixture comprises one or more unsaturated esters, which optionally are converted to the corresponding unsaturated carboxylic acids.

21. The process of claim 1 wherein the hydroxy-protected unsaturated fatty acid or fatty acid ester is prepared by treating a hydroxy-substituted unsaturated fatty acid or fatty acid ester with a hydroxy-protection reagent selected from the group consisting of carboxylic halides, anhydrides, alcohols, alkyl halides, and dialkyl carbonates, under conditions sufficient to prepare the hydroxy-protected unsaturated fatty acid or fatty acid ester.

22. A process of producing a homo-allylic mono-alcohol or homo-allylic polyol comprising (a) treating a hydroxy-substituted unsaturated fatty acid or fatty acid ester, wherein the hydroxy and unsaturated functions occupy a homo-allylic relationship, with a hydroxy-protection reagent under conditions sufficient to produce a hydroxy-protected unsaturated fatty acid or fatty acid ester; (b) contacting the hydroxy-protected unsaturated fatty acid or fatty acid ester with a metathesis catalyst, and optionally a lower olefin, under metathesis conditions sufficient to produce a product mixture comprising at least one hydroxy-protected unsaturated product that is different from the hydroxy-protected unsaturated fatty acid or fatty acid ester; (c) optionally, separating the hydroxy-protected unsaturated product from the product mixture; and (d) deprotecting the hydroxy-protected unsaturated product under conditions sufficient to prepare the homo-allylic mono-alcohol or homo-allylic polyol.

23. The process of claim 22 wherein the hydroxy-substituted unsaturated fatty acid ester is methyl ricinoleate; the homo-allylic mono-alcohol comprises 1-decene-4-ol; and the homo-allylic polyol comprises 9-octadecene-7,12-diol.

24. A composition comprising 9-octadecene-7,12-diol.

25. The composition of claim 24 prepared by a process comprising (a) converting 12-hydroxy-octadec-9-eneoic acid or an ester thereof into a corresponding 12-hydroxy-protected octadec-9-eneoic acid or ester thereof; (b) homo-metathesizing the 12-hydroxy-protected acid or ester in the presence of a metathesis catalyst under metathesis conditions sufficient to prepare a hydroxy-protected 9-octadecene-7,12 diol; and (c) deprotecting the hydroxy-protected unsaturated diol under conditions sufficient to prepare 9-octadecene-7,12-diol.

* * * * *